United States Patent
Adlassnig et al.

(10) Patent No.: US 7,442,289 B2
(45) Date of Patent: Oct. 28, 2008

(54) AMPEROMETRIC BIOSENSOR IN THICK FILM TECHNOLOGY

(75) Inventors: Alexander Adlassnig, Landstrasser Hauptstrasse 106, Vienna (AT) A-1030; Juliua Schuster, Vienna (AT)

(73) Assignees: Alexander Adlassnig, Vienna (AT); Julius Schuster, Vienna (AT)

( * ) Notice: Subject to any disclaimer, the term of this patent is extended or adjusted under 35 U.S.C. 154(b) by 803 days.

(21) Appl. No.: 10/486,300

(22) PCT Filed: Jul. 12, 2002

(86) PCT No.: PCT/EP02/07765

§ 371 (c)(1), (2), (4) Date: Feb. 9, 2004

(87) PCT Pub. No.: WO03/014378

PCT Pub. Date: Feb. 20, 2003

(65) Prior Publication Data

US 2004/0241746 A1  Dec. 2, 2004

(30) Foreign Application Priority Data

Aug. 9, 2001 (AT) ............................. A 1248/2001

(51) Int. Cl.
*G01N 27/327* (2006.01)

(52) U.S. Cl. ............... 205/778; 204/403.05; 106/31.92; 427/511

(58) Field of Classification Search ........................ 204/403.01–403.15; 205/777.5, 778, 792; 427/511; 106/31.92

See application file for complete search history.

(56) References Cited

U.S. PATENT DOCUMENTS

| | | | | |
|---|---|---|---|---|
| 5,567,301 A | | 10/1996 | Stetter et al. | 205/777.5 |
| 5,708,247 A | * | 1/1998 | McAleer et al. | 204/403.05 |
| 5,804,047 A | | 9/1998 | Karube et al. | 204/403 |
| 5,874,047 A | | 2/1999 | Schöning et al. | 422/82.02 |
| 5,951,836 A | * | 9/1999 | McAleer et al. | 205/777.5 |

(Continued)

FOREIGN PATENT DOCUMENTS

AT    397512    4/1994

(Continued)

OTHER PUBLICATIONS

Guiseppi-Elie et al. "Composite Hydrogels Containing Polypyrrole as support membranes for Amperometric Enzyme Biosensors" (2001) J. Macromol. Sci.—Pure Appl. Chem., A 38(12), 1575-1591.*

(Continued)

*Primary Examiner*—Kaj K Olsen
(74) *Attorney, Agent, or Firm*—Fulbright & Jaworski LLP

(57) ABSTRACT

Described is an amperometric biosensor in thick film technology for the detection an/or determination of substances undergoing enzyme catalyzed reactions, especially glucose or lactate, comprising an inert carrier material, at least one transducer layer exhibiting a specific electrical conductivity $\chi > 10^4 \ \Omega^{-1}\mathrm{cm}^{-1}$, and at least one bioactive layer with diffusion barrier function containing at least one enzyme specifically reacting with said substance to be measured, said bioactive layer exhibiting a specific electrical conductivity $\chi < 1 \ \Omega^{-1}\mathrm{cm}^{-1}$ and said bioactive layer further effectively hinders other electroactive substances to reach the transducer layer within the time of measurement.

9 Claims, 2 Drawing Sheets

U.S. PATENT DOCUMENTS 6,162,611 A * 12/2000 Heller et al. .................. 435/14
6,241,862 B1 * 6/2001 McAleer et al. ........ 204/403.05
6,939,450 B2 * 9/2005 Karinka et al. .............. 204/409

FOREIGN PATENT DOCUMENTS

| DE | 4212912 | 10/1993 |
|---|---|---|
| DE | 4427921 | 2/1996 |
| EP | 0691408 | 11/1994 |
| EP | 0634488 | 1/1995 |
| EP | 0652436 | 1/1995 |
| EP | 0987333 | 3/2000 |
| WO | WO 99/24824 | 5/1999 |

OTHER PUBLICATIONS

Albareda-Sirvent et al., "Configurations used in the design of screen-printed enzymatic biosensors: A review," *Sensors and Actuators,* Elsevier Sequoia, 69(1-2):153-163, 2000.

Whithe, "Thick Film Technology," In: Prudenziati (ed.) "Thick Film Sensors," Elsevier, Amsterdam, pp. 3ff., 1994.

* cited by examiner

AMPEROMETRIC BIOSENSOR IN THICK FILM TECHNOLOGY

This application is a national phase application under 35 U.S.C. §371 of PCT Application No. PCT/EP02/07765 filed 12 Jul. 2002, which claims priority to Austrian Application No. A 1248/2001 filed 9 Aug. 2001, the contents of which are incorporated herein by reference in their entirety.

This present invention relates to biosensors in thick film technology for the selective detection and/or determination of substances undergoing enzyme catalyzed reactions, to processes to manufacture such biosensors, to screen printing inks suitable for such processes, and to the synthesis of such printing inks.

Biosensors are based on the coupling of one or more biochemically active substances having high selectivity (e.g. enzymes, antibodies etc.) with a physico-chemical transducer followed by electronic signal processing and/or display. Amperometric sensors are used for applications with low detection limits ($\geqq 10^{-8}$ mol/l) and linear measurement ranges across up to 6 concentration decades. They are based on heterogeneous electron transfer reactions between the bioactive substances and the transducer. The electrical communication occurs via so called mediators. A naturally available candidate for the function of mediator is the reaction product between the bioactive substance and the substance of interest in the analyte. In complex analytes containing additional electroactive substances presently known biosensors suffer from signal interference if these substances are capable of reaching the transducer. One concept to solve this problem involves the addition of alternate mediators, which have a lower overvoltage at the electrode and are thus reacting at lower potentials than the interfering substances. Using such alternate mediators permits the use of graphite as transducer. It is common to use graphite, a bioactive substance, and a solvent with other additives to obtain a screen printable ink. This permits to take advantage of the screen printing technology (e.g. device structuring, economic mass production etc.) in producing the bioactive layer of sensors. Using small and mobile molecules as alternate mediators, however, introduces the problem that they are either water soluble and thus leached from the bioactive layer during the measurement (e.g. hexacyanoferate, hydrochinone), or that they are toxic and thus critical for in vivo applications (e.g. vinylferrocene). Thus it was proposed to avoid the problem of leaching by covalently binding the mediator to the bioactive substance (U.S. Pat. No. 5,804,047). As far is known, sensors produced by this method have an insufficient small linear measurement range. Alternatively, it has been proposed to bind the mediator covalently to the transducer (AT 397512 B). In the latter case, however, the bioactive layer is not produceable by screen printing.

There is another concept in biosensor technology which avoids such alternate mediators (and the accompanying problems): Additional membranes are placed either between the analyte and the bioactive layer or between the bioactive layer and the electrode. The first configuration may form an effective diffusion barrier (i.e. the interfering substances does not alter significantly the signal within the time of measurement) for all interfering substances but the substance of interest in the analyte, the latter for all interfering substances but the mediator. In order to form such an effective diffusion barrier layer thicknesses around 100 nm typically realizable by drying liquid films (produced e.g. by dip-coating once) or drops are insufficient. Thick film technology, on the other hand, permits to realize membranes having layer thicknesses $\geqq 5$ μm in a single production step. As mentioned above, previously published thick film ink formulations for bioactive and/or biocompatible layers in biosensors always contain graphite, which in addition functions as transducer. Such inks are thus not suitable to realize a diffusion barrier between the bioactive substance and the transducer. Without the addition of graphite, however, formulations described up to now are not screen printable, and thus a layer sufficiently thick to form an effective diffusion barrier cannot be obtained in a single production step.

It is therefore an object of the present invention to provide improved thick film technology biosensors. Such improved biosensors should preferably be robust, easily produceable also on an industrial scale and, this would specifically be preferred, graphite free.

Therefore, the present invention provides an amperometric biosensor in thick film technology for the detection an/or determination of substances undergoing enzyme catalyzed reactions, especially glucose or lactate, comprising an inert carrier material, at least one transducer layer exhibiting a specific electrical conductivity $\chi > 10^4$ $\Omega^{-1} \text{cm}^{-1}$, serving as electrode, transducer, etc., and at least one bioactive layer with diffusion barrier function containing at least one enzyme specifically reacting with said substance to be measured, said bioactive layer exhibiting a specific electrical conductivity $\chi < 1 \Omega^{-1} \text{cm}^{-1}$ and said bioactive layer further effectively hinders other electroactive substances to reach the transducer layer within the time of measurement.

The invention combines the advantages of biosensors (such as e.g. high specivity in complex media) with the advantages of thick film technology (such as e.g. high flexibility in sensor design, easy integration into electrical circuits, mass producible in standardized quality). This permits the economic production of sensors for applications in food, biological, pharmaceutical, and medical analysis. Furthermore, the invention can be employed for monitoring applications ranging from body functions, to bioreactors, or to the environment.

For immobilisation of the bioactive substance(s) (such as e.g. enzymes) in the bioactive layer the use of one or more biocompatible polymers and/or inorganic gels permits to avoid components in the printing ink, which are necessary to obtain printability but are detrimental for the formation of an affective diffusion barrier between the analyte and the transducers against interfering electroactive substances.

The production of graphite free, bioactive layers in thick film technology according to the present invention eliminates the occurrence of interfering signals caused by other electrode active substances present in complex analytes without the need to employ alternate mediators.

The production of all sensor layers including the bioactive layers in thick film technology straightforward permits structuring of miniaturized multisensor arrays. This increases significantly the reliability of the device by structuring several identical sensors in parallel, as well as the selectivity of the device by logical combination of several not identical sensors.

The production of the bioactive layer in thick film technology eliminates problems of inhomogenity in bioacitvity and thus sensitivity. These occur frequently with sensors produced according to the current state of the art (using e.g. dip coating etc.). Due to the low cost of (and thus in the electronics industry well established) thick film technology "use once and dispose"—applications can be realized, which up to now could not be considered due to unfavorable economics.

The biosensor according to the present invention may comprise at least one bioactive layer with diffusion barrier function consisting of two or more zones, of which the zone adjacent to the electrically conducting layer is preferably depleted of bioactive substances. However, it is also preferred to use bioactive layer(s) with homogeneously distributed enzymes contained therein.

According to a further aspect, the present invention relates to a process for producing a biosensor according to the present invention which is characterized in that at least one bioactive layer with diffusion barrier function is produced by screen printing. The present invention therefore also relates to a process for producing a biosensor according to the present invention, characterized by the following steps providing an inert carrier material, depositing at least one electrically conducting layer on this inert carrier material and depositing at least one bioactive layer with diffusion barrier function onto the at least one electrically conducting layer by screen printing using a transducer-free printing ink containing an enzyme and a biocompatible polymer.

Preferably, at least one bioactive layer is synthesized from a printing ink, which contains at least one bioactive substance, but is free of components, which act as transducers.

Moreover, the present invention relates to a printing ink containing a bioactive substance, especially an enzyme, characterized in that it is screen printable as well as forming bioactive layers with diffusion barrier function as defined above.

The printing inks according to the present invention conform:

(a) with the requirements of the screen printing process (regarding e.g. rheology, adhesion on the substrate etc.), and after this step form (b) membranes meeting the requirement of the biosensors of interest (regarding e.g. bioactivity, selectivity, sensitivity, homogeneity, reliability etc.).

As defined above, the present invention relates to an amperometric biosensor with the following preferred set-up: On an inert carrier (e.g. $Al_2O_3$) a working electrode, counter electrode, and reference electrode, as well as the necessary electrical connections are deposited (preferably using screen printing (as e.g. referred to in Whithe "Thick Film Technology" in Prudenziati (Ed.) "Thick Film Sensors" (Elsevier, Amsterdam, 1994) pp 3ff.)), dried and fixed (by e.g. sintering). Onto the working electrode a coating of graphite free bioactive material having $\geq 5$ μm layer thickness is deposited (preferably using screen printing) and dried. This so formed bioactive layer contains bioactive substances (such e.g. one or more enzymes, preferably oxidases.) which are immobilized without the use of heat and UV-radiation by gel entrapment in at least one biocompatible polymer or inorganic gel (preferably polyHEMA, $SiO_2$).

Putting this bioactive layer in contact with an analyte, which contains the substrate of at least one of the enzymes immobilized in the layer (such as e.g. glucose for glucose oxidase), this substrate diffuses into the layer until it is enzymatically reacted. The reaction product (e.g. $H_2O_2$) functions as mediator formed in situ and diffuses to the working electrode serving as transducer.

For such "in situ" mediators the diffusion rates in the biocompatible polymer or inorganic gel selected for the production of the bioactive layer (preferably polyHEMA, $SiO_2$) are higher, than the diffusion rates of other electrode active substances (such as e.g. ascorbic acid), which are typically present in complex analytes and cause interfering sensor signals at the potential required to detect the "in situ" mediator.

Thus, a (polymer and/or gel) layer having $\geq 5$ μm thickness forms an effective diffusion barrier for such interfering substances and assures that within the time of measurement the sensor signal is specifically caused by the in "situ" mediator. Producing the bioactive layer in thick film technology effects that the sensor signal selectively is due to the bioreaction of interest (e.g. oxidation of glucose by glucose oxidase).

In case the substrate for the enzymatic reaction, too, is subjected to the above described diffusion barrier effect, it may be favorable to add bioactive substances (e.g. enzymes etc.) only to the zone of the bioactive layer adjacent to the analyte, and to reduce its content in the zone adjacent to the transducer. This technologically more complex production process results in advantageous material cost reduction in the case expensive bioactive substances are involved.

Using screen printing for the production of the bioactive layer results in the advantage, that the structuring of the sensor components can be effected with significant higher resolution ($\leq 10$ μm) than with processes, which are based on drying of a liquid film or droplet (such as e.g. dip-coating). This capability of the screen printing technology to mass produce cost efficiently sensor arrays consisting of several miniaturized identical sensors in parallel increases significantly the reliability of the device, because the production related non-function of one individual sensor does not cause the failure of the entire device. The just as well cost efficient mass producible logic combination to an array of several miniaturized not identical sensors permits the combined detection/determination of more than one substance in the analyte and thus an increase in selectivity beyond one single bioreaction. This results in a decisive support for the diagnosis of medical and biological phenomena.

Producing the bioactive layer by screen printing allows reproducible control of the homogeneity of the bioactive substance distribution therein. This permits to avoid inhomogenities, which derive from drying of layers made by dip-coating or related processes, and which leads to unfavorable variations in sensitivity in so far known sensors.

The screen printing ink, from which sensors characterized by such advantageous bioactive layers are made, consists at least of (a) one or more bioactive substance (e.g. enzyme, preferably oxidase) in buffered environment, (b) one or more biocompatible inorganic or organic substance (e.g. biocompatible polymer, preferably polyHEMA; inorganic gel former, preferably one or more silicate, aluminate, their hydrate, hydroxide, alcoholate etc.) to adjust the rheological properties required for the screen printing process (e.g. viscosity, thixotropy etc.), and (c) a solvent or mixture of solvents (e.g. water, alcohols, glycols, polyglycols etc.) which do not physically or chemically cause deactivation of the bioactive substance(s).

Such inks according to the present invention are free of components which act as transducer. Since so far all screen printed bioactive layers contain graphite, they do not form effective diffusion barriers against interfering substances from the analyse, and sensors made thereof require the addition of alternate mediators for a selective signal. According to the present invention these are no more needed.

The preparation of the above described ink advantageously is done by separate preparation and consecutive controlled unification of solutions of the biocompatible polymer, inorganic gel former, and buffered bioactive substance. To prepare solutions of the polymer as well as the inorganic gel former either a previously "ex situ" synthesized thickening agens (e.g. polyHEMA) may be used, or the thickening agens may be synthesized "in situ" from the components (e.g. inorganic gel forming oxides, hydroxides, hydrates or alcoholates of Al, B, Ca, Fe, K, Na, Mg, Si, Ti).

The invention is further described in the following examples and the drawing figures, yet without being restricted thereto.

EXAMPLES

Example 1

Synthesis of a Glucose Oxidase Printing Ink

A polymer solution consisting of 6.625 mass parts polyHEMA (polymerized hydroxy ethylene metacrylate, molecular weight ~45000), 59.581 mass parts diethylene glycol (DEG), and 33.794 mass parts water is combined with 14.959 mass parts $SiO_2$ gel former. To this solution 720 U/(g ink) glucose oxidase (GOD, EC 1.1.3.4.), are added, typically dissolved in 50 mM potassium phosphate buffer pH 7.0 made by mixing of 50 mM $KH_2PO_4$ and 50 mM $K_2HPO_4$ with water (the pH of the potassium phosphate buffer is adjusted using 3M NaOH). This ink is directly screen printable or storable at 4° C.

Example 2

Synthesis of a Lactate Oxidase Printing Ink

To a polymer and inorganic gel solution described in Example 1 380 U/(g ink) lactate oxidase (LOD, EC 1.1.3.2.), are added, typically dissolved in 50 mM potassium phosphate buffer pH 7.0 made by mixing of 50 mM $KH_2PO_4$ and 50 mM $K_2HPO_4$ with water (the pH of the potassium phosphate buffer is adjusted using 3M NaOH).

This ink is directly screen printable or storable at 4° C.

Example 3

Synthesis of a Glucose Oxidase Printing Ink

To a polymer solution described in Example 1 3.506 mass parts $SiO_2$, 0.800 mass parts $Al_2O_3$, 0.040 mass parts $Fe_2O_3$/FeO, 0.011 mass parts $TiO_2$, 0.185 mass parts MgO, 0.080 mass parts CaO, and 0.014 mass parts $Na_2O$ gel former are added. Then a glucose oxidase solution described in Example 1 is added. This ink is directly screen printable or storable at 4° C.

Example 4

Synthesis of a Lactate Oxidase Printing Ink

To a polymer solution described in Example 1, a gel former described in Example 3 is added. Then a lactate oxidase solution described in Example 2 is added. This ink is directly screen printable or storable at 4° C.

Example 5

Rheological Behaviour of a Screen Printable Glucose Oxidase Printing Ink

Figure 1:
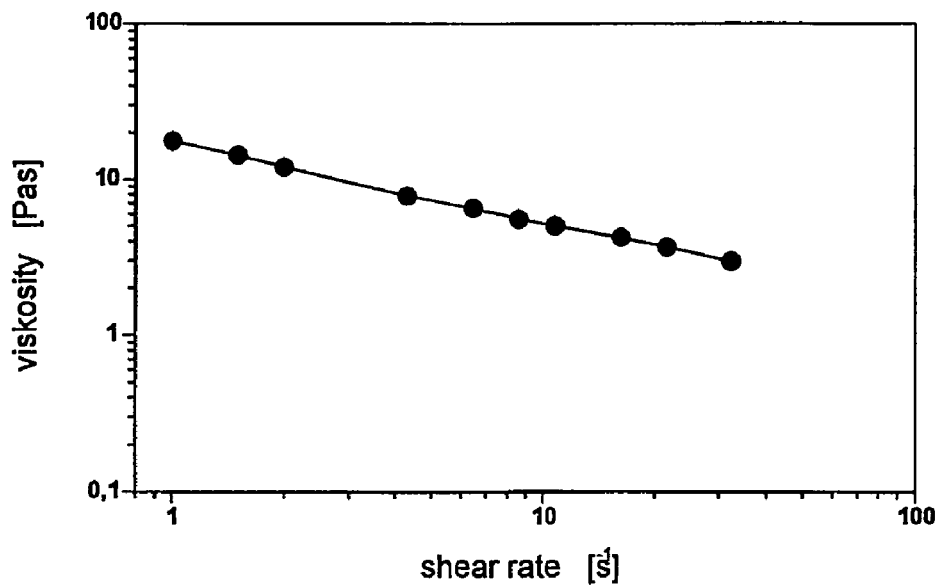
FIG. 1 shows the rheological behaviour of a printing ink according to the present invention.

A screen printing ink consisting of 66.63 mass parts polyHEMA, 89.326 mass parts diethylene glycol, and 4.011 mass parts water, 14.959 mass parts $SiO_2$ gel former, and 720 U/(g ink) glucose oxidase (GOD, EC 1.1.3.4.), typically dissolved in 50 mM potassium phosphate buffer pH 7.0 made by mixing of 50 mM $KH_2PO_4$ and 50 mM $K_2HPO_4$ with water (the pH of the potassium phosphate buffer is adjusted using 3M NaOH), has the rheological behaviour shown in FIG. 1 and is therefore suitable for screen printing.

Example 6

Synthesis of a Bioactive Layer Having Controlled Layer Thickness by Screen Printing A screen printing ink according to e.g. Example 1 is placed on top of the screen of a screen printing machine, and evenly spreaded out. The ink is then forced through the screen by a squeegee, is allowed to level and dry. The thickness of the bioactive layer can be controlled by the drying parameters (Table 1).

TABLE 1

| Variation of the layer thickness with the drying temperature ||
|---|---|
| drying conditions | layer thickness |
| 3 days 4° C. | 37 μm |
| 3 days room temperature | 23 μm |
| 3 days 37° C. | 22 μm |
| 3 days 80° C. | 19 μm |

Example 7

Bioactive Glucose Oxidase Thick Film Layer

Figure 2:
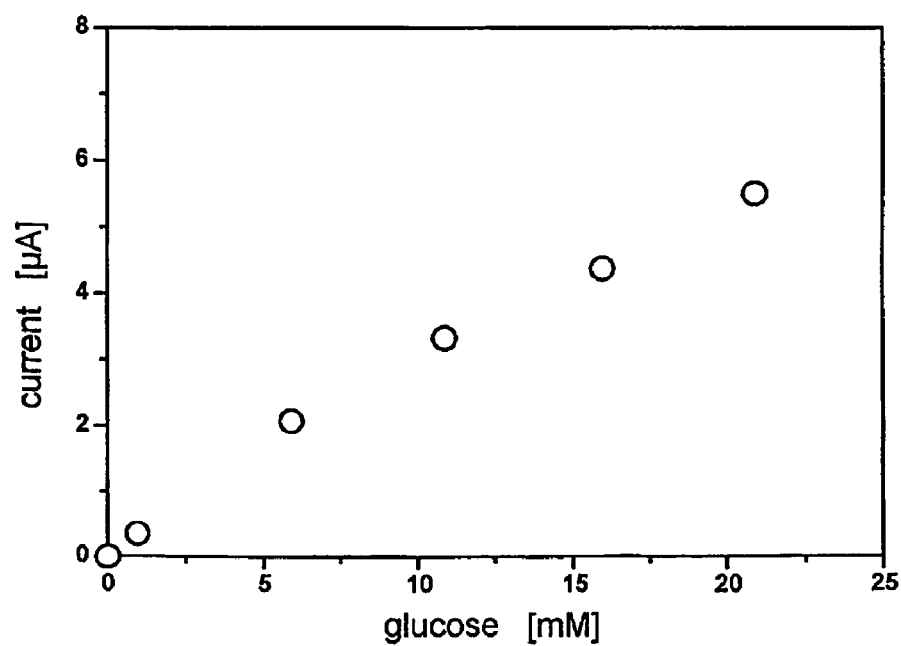
FIG. 2 shows the correlation of glucose concentrations with current.

A sensor with a bioactive layer produced according to Example 6 from a screen printing ink described in Example 1, contains GOD with an activity of 80% of the starting activity. The sensor signal is in the μA range, is stable after 20 seconds, and is linear for glucose concentrations between 0 and 20 mM (FIG. 2), covering quantitatively the range of physiological interest.

Example 8

Selectivity of the Bioactive Thick Film Layer With GOD

Figure 3:
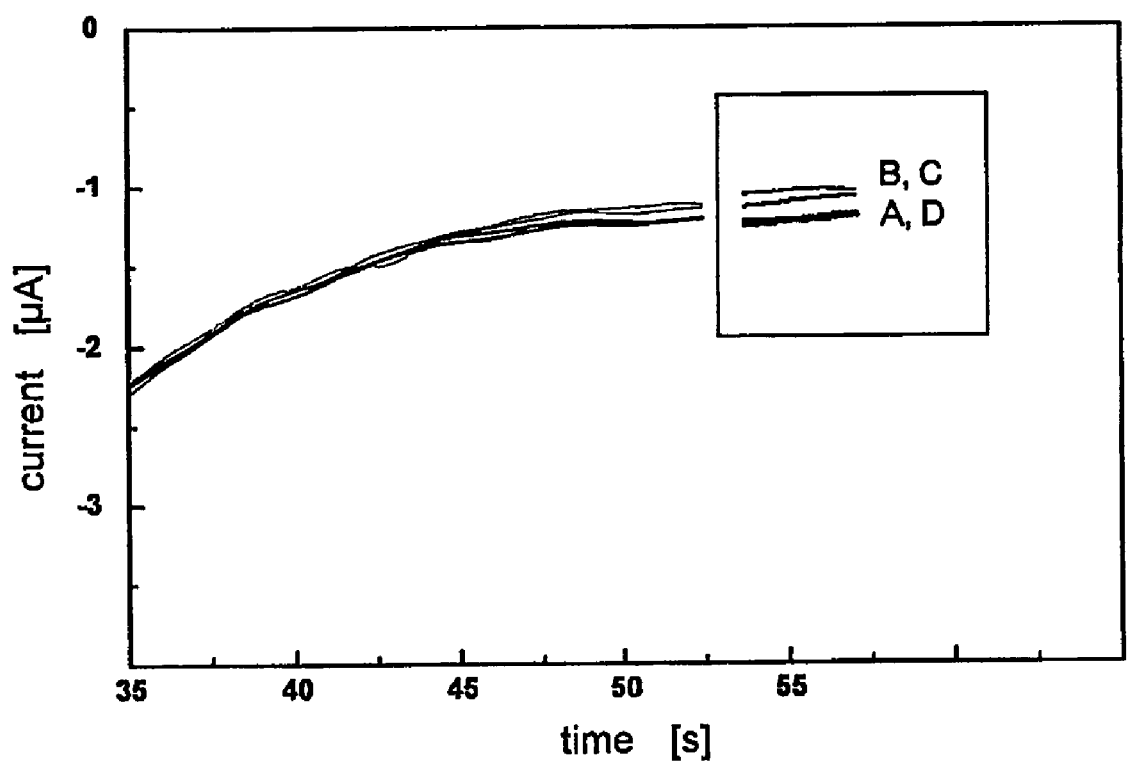
FIG. 3 shows the selectivity of the potentiostatically measured signal of a biosensor according to the present invention

A biosensor with a thick film layer according to Example 7 gives a specific signal for glucose. This signal is not affected by interfering substances such as e.g. ascorbic acid, urea, glycine or paracetamol. FIG. 3 shows the signal for such an electrode measured potentiostatically. Curve A: analyte with 5mM glucose (typical physiological concentration in blood) an no interfering substances; curve B: analyte with 5 mM glucose plus 60 μM ascorbic acid (maximum physiological concentration in blood); curve C: analyte with 5 mM glucose plus 25 mM urea (5-fold of the typical concentration in blood), curve D: analyte with 5 mM glucose plus 2,5 mM paracetamol (15-fold of the maximum concentration in blood of an arthrosis patient medicated with this drug). Even if the figure is magnified (insert in FIG. 3) all curves are identical within the experimental accuracy.

The invention claimed is:

1. A thick film amperometric biosensor capable of detection and/or determination of a substance undergoing an enzyme-catalyzed reaction comprising:

an inert carrier material;

at least one transducer layer exhibiting a specific electrical conductivity $\chi > 10^4 \Omega^{-1} cm^{-1}$, during use of the biosensor; and at least one bioactive layer adapted to function as a diffusion barrier during use of the biosensor, the bioactive layer further defined as:

comprising at least one enzyme capable of specifically reacting with the substance to be detected or determined during use of the biosensor;

exhibiting a specific electrical conductivity of $\chi<1\Omega^{-1}cm^{-1}$ during use of the biosensor; and capable of effectively hindering electroactive substances, other than any produced by the substance undergoing the enzyme-catalyzed reaction, from reaching the transducer layer during use of the biosensor.

2. The biosensor of claim 1, further defined as adapted for the detection and/or determination of glucose or lactate undergoing an enzyme-catalyzed reaction.

3. The biosensor of claim 1, wherein the at least one bioactive layer comprises two or more zones.

4. The biosensor of claim 3, wherein at least one of the at least two or more zones is a zone adjacent to the electrically conducting layer that is depleted of bioactive substances.

5. A process for producing a thick film amperometric biosensor capable of detection and/or determination of a substance undergoing an enzyme-catalyzed reaction comprising:

providing an inert carrier material;

depositing at least one electrically conducting layer on the inert carrier material; and depositing at least one bioactive layer capable of functioning as a diffusion barrier during use of the biosensor onto the at least one electrically conducting layer by screen printing using a transducer-free printing ink comprising an enzyme and a biocompatible polymer, this depositing being accomplished without the use of UV-radiation, wherein the bioactive layer is capable of effectively hindering electroactive substances, other than any produced by the substance undergoing the enzyme-catalyzed reaction, from reaching the transducer layer during use of the biosensor.

6. The process of claim 5, wherein the at least one bioactive layer is produced from a printing ink that comprises at least one bioactive substance but is free of components that could act as transducers during use of the biosensor.

7. A printing ink comprising an enzyme, wherein the ink is screen printable without the use of UV-radiation and capable of, in an amperometric biosensor capable of detection and/or determination of a substance undergoing an enzyme-catalyzed reaction, forming at least one bioactive layer, adapted to:

function as a diffusion barrier during use of the biosensor;

have a specific electrical conductivity of $\chi<1\ \Omega^{-1}cm^{-1}$ during use of the biosensor; and effectively hinder electroactive substances other than any produced by the substance undergoing the enzyme-catalyzed reaction from reaching a transducer layer during use of the biosensor.

8. The printing ink of claim 7, further defined as free of components that could act as transducers during use of the biosensor.

9. A method of detection and/or determination of a substance undergoing an enzyme-catalyzed reaction comprising:

obtaining a thick film amperometric biosensor capable of detection and/or determination of a substance undergoing an enzyme-catalyzed reaction comprising: (a) an inert carrier material; (b) at least one transducer layer exhibiting a specific electrical conductivity $\chi>10^4\ \Omega^{-1}cm^{-1}$, during use of the biosensor; and (c) at least one bioactive layer adapted to function as a diffusion barrier during use during use of the biosensor, the bioactive layer further defined as: (i) comprising at least one enzyme capable of specifically reacting with the substance to be detected or determined during use of the biosensor; (ii) exhibiting a specific electrical conductivity of $\chi<1\ \Omega^{-1}cm^{-1}$ during use of the biosensor; and (iii) capable of effectively hindering electroactive substances, other than any produced by the substance undergoing the enzyme-catalyzed reaction, from reaching the transducer layer during use of the biosensor;

obtaining a sample; and using the biosensor to detect and/or determine a substance in the sample.

\* \* \* \* \*

UNITED STATES PATENT AND TRADEMARK OFFICE
CERTIFICATE OF CORRECTION

PATENT NO. : 7,442,289 B2
APPLICATION NO. : 10/486300
DATED : October 28, 2008
INVENTOR(S) : Alexander Adlassnig et al.

Page 1 of 1

It is certified that error appears in the above-identified patent and that said Letters Patent is hereby corrected as shown below:

In title page, item (75) Inventors, line 3, delete "Juliua" and insert --Julius-- therefor.

In title page, item (57) Abstract, line 6, delete "$\Omega\text{-}^1\text{cm-}^1$" and insert --$\Omega^{-1}\text{cm}^{-1}$-- therefor.

In title page, item (57) Abstract, line 10, delete "$\Omega\text{-}^1\text{cm-}^1$" and insert --$\Omega^{-1}\text{cm}^{-1}$-- therefor.

In claim 14, column 8, line 28, delete "during use during use" and insert --during use-- therefor.

Signed and Sealed this

Thirteenth Day of January, 2009

JON W. DUDAS
*Director of the United States Patent and Trademark Office*